US012578325B2

(12) United States Patent
Zhang

(10) Patent No.: US 12,578,325 B2
(45) Date of Patent: Mar. 17, 2026

(54) STAINING METHOD FOR LIVE-CELL IMAGING

(71) Applicant: huimin Zhang, Shanghai (CN)

(72) Inventor: huimin Zhang, Shanghai (CN)

( * ) Notice: Subject to any disclaimer, the term of this patent is extended or adjusted under 35 U.S.C. 154(b) by 782 days.

(21) Appl. No.: 17/786,532

(22) PCT Filed: Jun. 1, 2021

(86) PCT No.: PCT/CN2021/097587
  § 371 (c)(1),
  (2) Date: Jun. 17, 2022

(87) PCT Pub. No.: WO2022/252104
  PCT Pub. Date: Dec. 8, 2022

(65) Prior Publication Data
  US 2023/0176039 A1    Jun. 8, 2023

(51) Int. Cl.
  *G01N 1/00*      (2006.01)
  *G01N 1/30*      (2006.01)
  *G01N 21/64*     (2006.01)
  *G01N 33/50*     (2006.01)

(52) U.S. Cl.
  CPC ........... *G01N 33/5091* (2013.01); *G01N 1/30* (2013.01); *G01N 21/6428* (2013.01); *G01N 21/6458* (2013.01); *G01N 2001/302* (2013.01); *G01N 2021/6441* (2013.01)

(58) Field of Classification Search
  CPC ...................................................... G01N 1/30
  See application file for complete search history.

(56) References Cited

U.S. PATENT DOCUMENTS

| | | |
|---|---|---|
| 9,625,387 B2 | 4/2017 | Demos et al. |
| 10,391,330 B2 * | 8/2019 | Bourke, Jr. ............... A61P 9/10 |
| 2011/0183370 A1 | 7/2011 | Noiseux et al. |
| 2015/0330892 A1 * | 11/2015 | Cerignoli ........... G01N 21/6458 348/79 |
| 2019/0046479 A1 * | 2/2019 | Pathak .............. A61M 37/0076 |
| 2019/0358348 A1 | 11/2019 | Abbaci et al. |

FOREIGN PATENT DOCUMENTS

| | | | |
|---|---|---|---|
| CN | 108007754 A | * | 5/2018 |
| CN | 103712967 A | | 12/2019 |

OTHER PUBLICATIONS

Moore et al. Determination of cell nucleus-to-cytoplasmic ratio using imaging flow cytometry and a combined ultrasound and photoacoustic technique: a comparison study. J Biomed Opt. Oct. 2019;24(10):1-10. (Year: 2019).*

Mpoke et al. Differential Staining of Apoptotic Nuclei in Living Cells: Application to Macronuclear Elimination in Tetrahymena. 2019, J Biomed Opt. 45(5): 675â683. (Year: 2019).*

* cited by examiner

*Primary Examiner* — Jyoti Nagpaul

(57) ABSTRACT

The present invention provides a fluorescent staining method for live-cell imaging. First, cells are double stained through the first and second fluorescent biomarker. Then, the clear fluorescent cell image is shown under a fluorescent microscope, and we can observe the nucleus form while observing the cell form through the obtained image.

15 Claims, 8 Drawing Sheets

STAINING METHOD FOR LIVE-CELL IMAGING

TECHNICAL FIELD

The present disclosure generally relates to a staining method for cell imaging, particularly to a double-staining method of using fluorescent biomarkers. It belongs to the field of biotechnology.

BACKGROUND OF THE INVENTION

The combination of fluorescent staining methods and microscopic technology makes fluorescent images widely used to detect biologically active substances and cell imaging. Cell imaging technology is an important research method in the field of life science and technology. Compared with other technologies, fluorescent staining has the advantages of high sensitivity, high selectivity, simple operation, and sensitive response. It is currently a high-sensitive visual analysis technology widely used in the live-cell analysis.

Fluorescence is a kind of "photoluminescence", which is a form of luminescence. When a particular normal temperature substance is illuminated by the incident light of a specific wavelength, it enters the exciting state after absorbing the light energy. It immediately emits emergent light with a longer wavelength than incident light. The emergent light with this characteristic is called fluorescence.

The fluorescent spectrum includes two types: excitation spectrum and emission spectrum. The excitation spectrum refers to the relationship between a certain emission spectrum line and the band strength, or the relationship between luminous efficiency and excitation wavelength when the fluorescent substance is stimulated by different wavelength light. The emission spectrum refers to the strong and weak changes of the luminous intensity at different wavelengths when the fluorescent substance is stimulated by certain excitation light. Each fluorescent substance has an excitation spectrum and emission spectrum and its most suitable stimulating band and launch band. Fluorescence research mainly studies fluorescent substances' excitation spectrum and emission spectrum to find their most suitable stimulating bands and launch bands, such as 5-aminolevulinic acid (5-ALA), which is widely used in clinical practice applications.

Using 5-ALA to detect malignant lesions is currently clinically applied to neurosurgery, urology, and gastroenterology. Using protoporphyrin IX (PP IX), which 5-ALA induces, became the promising fluorescent detect method of malignant lesions during surgery. In order to improve the detection accuracy of 5-ALA under strongly spontaneous fluorescent conditions, there are several spectral analysis methods (Valdes, P. A. et al. (2011) Neurosurg. 115, 11-17; Xu, H. & Rice, B. W. (2009) Journal of biomedical optics 14, 064011; Harada, K. et al, (2013) International Journal of Molecular Sciences 14, 23140-23152; Koizumi, N. et al. (2013) Ann. Surg. Oncol. 20, 3541-3548; Krondo, Y. et al. (2014) Int. J. Oncol. 45, 41-46), Although some studies have reported the effectiveness of the 5-ALA fluorescent detection method in clinical applications, detection errors often occur due to the strong fluorescence background of the chromophore.

Some fluorescent biomarkers have been studied. In addition to the 5-ALA, at the moment fluorescein sodium (FS) and indocyanine green (ICG) are widely used.

Fluorescein sodium is a living fluorescent dye. Its aqueous solution can mark cell body contours and improve the tumor tissue visualization, and fluorescein sodium has no specificity to tumor cells. When this dye is stimulated by the wavelength in the range of 460-500 nm, it will emit fluorescence radiation with a wavelength in the range of 540-690 nm. It is applied widely in medicine, especially in brain tumor surgery (Copeman S M, Coke F, Gouldesbrough C., Br Med J. (1929) 2:233-42; Hamamcioglu M K. et al., Clin Neurol Neurosurg (2016) 143:39-45; O'goshi K, Serup J., Ski Res Technol. (2006) 12:155-61; Koc K. et al., Br J Neurosurg (2008) 22:99-103; Hara T. et al., Am J Ophthalmol. (1998) 126:560-4; Kuroiwa T. et al., Surg Neurol (1998) 50:41-8).

Indocyanine green (ICG) is a small amphiphile (<800 Dalton), a near-infrared spectrum (NIR) fluorophore (peak stimulation=805 nm, peak emission=835 nm). After intravenous injection, ICG usually stays in the blood vessels, and mainly combines with albumin and other plasma proteins to perform near-infrared imaging to depict the vascular system. In recent years, ICG has been found in the study of tumor tissue in rats and human patients. ICG has accumulated in tumors and has significant contrast between tumors and backgrounds. ICG has been proved to have practical value in marking tumor tissue (Cho S S. et al., (2019) front. Surg. 6:11; Hansen Da et al., Surg Neurol.; Haglund mm., Et al., Neurosurgery. (1996) 38: 308-17; Madajewski B., et al., CLIN CANCER Res., AM J NUCL Med Mol Imaging. (2015) 5: 390-400; Zeh R. Et Al., Plos One. (2017) 12: E0182034).

Methylene blue (MB) is a dye approved by the United States Food and Drug Administration for methemoglobinemia treatment. It is a non-toxic alternative dye, In addition to ICG, MB is a near-infrared fluorophore available in human clinical trials. It emits at 700 nm in different near-infrared bands from fluorescein sodium and ICG.

Although the current research and application of fluorescent dyes are very broad, the staining effect of these fluorescent dyes is still insufficient. For example, there is no specificity between fluorescein sodium and ICG. 5-ALA specificity is higher than fluorescein sodium, but its sensitivity is not high, and it contrasts weakly with surrounding normal tissues (Okuda T. et al., J Clin Neurosci. (2012) 19:1719-22; Acerbi F. et al., Neurosurg. Focus. (2014) 36: E5; Okuda T. et al.. J Clin Neurosci. (2010) 17:118-121; 35. Chen B. et al., Int J Med Sci. (2012) 9:708-714; Francaviglia N. et al., Surg Neurol Int. (2017) 8:145; Bowden SG. et al., Neurosurgery. (2018) 82:719-27). Some studies have tried the dual injection of 5-ALA and fluorescein. By increasing contrast between the tumor tissue with 5-AT A and the peritumoral area with fluorescein to enhance the detection of tumor tissue (Suerso Molina F. et al., J Neurosurg. (2018) 128:399-405). The detection effect is improved, but it is still insufficient to meet clinical needs.

As we explained above, fluorescent staining agents are widely applied in clinical practice. Cell clumps first absorb dyes or staining agents, and they transform the agents. The agents combine with "photoluminescence" of luminescence to form fluorescent imaging and easily observe overall tissue. When observing live cells under a fluorescent microscope, these staining agents can only be absorbed by the cell body or nucleus for a single cell. During staining live cells and observing under a fluorescent microscope, using either acriflavine or fluorescein sodium can observe the nucleus forms, but the cell forms cannot be observed. We can only observe the nucleus form or the cell form under the microscope, and the agents do not the need to observe the nucleus forms and the cell forms simultaneously for cell observation.

In summary, fluorescent staining methods commonly used in live-cell imaging analysis need to fix the cells in the actual application. Furthermore, there are disadvantages, such as complicated use process, long staining process, no specificity staining, lack of contrast, and not clear enough to overserve forms of cell and nucleus at the same time. Therefore, improving the selectivity and accuracy of visual analysis is an urgent need to solve.

SUMMARY OF THE INVENTION

The main object of the present invention is to provide a new staining method. It uses fluorescent biomarkers to dual-stain live cells and overcomes the shortcomings of the prior art.

To solve the mentioned objective problem, the present invention provides the following technical solutions:

In one aspect, the present disclosure relates to a method for staining live cells. The method includes the following steps: simultaneously or separately(i) using the first fluorescent biomarker to stain the target cell; (ii) using the second fluorescent biomarker to stain the target cells; (iii) using a fluorescent microscope to obtain the fluorescent image of the target cells, which can observe the nucleus form while observing the cell form.

In one embodiment, the first fluorescent biomarker has a 460-800 nm excitation wavelength.

In one embodiment, the second fluorescent biomarker has a 350-670 nm excitation wavelength.

In one embodiment, the maximum value of the emission spectrum of the second fluorescent biomarker is at least 50 nm different from the maximum value of the excitation spectrum of the said first fluorescent biomarker.

In one embodiment, the first biomarker emits light and the second biomarker absorbs light when using a fluorescent microscope to obtain the fluorescent images of the target cells, In one embodiment, the first fluorescent biomarker is selected from fluorescein sodium, 5-aminolevulinic acid, and indocyanine green.

In one embodiment, the second biomarker is selected from methylene blue, acriflavine and crystal violet.

In yet another embodiment, the first biomarker is fluorescein sodium, and the second biomarker is methylene blue.

In a further embodiment, the concentration of fluorescein sodium is 0.1%-1%, and the concentration of methylene blue is 0.5%-3%.

In a further embodiment, the concentration of fluorescein sodium is 0.25%, and the concentration of methylene blue is 1%.

In yet another embodiment, the first biomarker is 5-aminolevulinic acid, and the second biomarker is acriflavine.

In a further embodiment, the concentration of 5-aminolevulinic acid is 0.05%, and the concentration of acriflavine is 1%.

In vet another embodiment, the first biomarker is indocyanine green, and the second biomarker is crystal violet.

In a further embodiment, the concentration of indocyanine green is 0.05%, and the concentration of crystal violet is 0.05%.

In one embodiment, the method is applied to live tissue staining.

In one embodiment, the live cells include tumor cells.

In one embodiment, the first fluorescent biomarker and the second fluorescent biomarker are applied to the affected area before surgery.

In a further embodiment, the surgery is cancer surgery.

In another aspect, the present disclosure relates a composition for live cell staining. The composition includes the first biomarker and the second biomarker.

In one embodiment, the first fluorescent biomarker is selected from fluorescein sodium, 5-aminolevulinic acid, and indocyanine green.

In one embodiment, the second biomarker is selected from methylene blue, acriflavine and crystal violet.

In yet another embodiment, the first biomarker is fluorescein sodium, and the second biomarker is methylene blue.

In a further embodiment, the concentration of fluorescein sodium is 0.1%-1%, and the concentration of methylene blue is 0.5%-3%.

In a further embodiment, the concentration of fluorescein sodium is 0.25%, and the concentration of methylene blue is 1%.

In yet another embodiment, the first biomarker is 5-aminolevulinic acid, and the second biomarker is acriflavine.

In a further embodiment, the concentration of 5-aminolevulinic acid is 0.05%, and the concentration of acriflavine is 1%.

In yet another embodiment, the first biomarker is indocyanine green, and the second biomarker is crystal violet.

In a further embodiment, the concentration of indocyanine green is 0.05%, and the concentration of crystal violet is 0.05%.

In a further embodiment, the composition further includes stabilizers, antioxidants, protectives, preservatives, and pH regulators.

In another aspect, the present disclosure relates to a composition using one or more physiological acceptable vehicles. The vehicles include excipients and auxiliary agents, which help to process the active agent into a medicinal preparation. Proper formulation depends on what the application is selected.

The stabilizers can be selected from one or more of polysorbate, ethoxylated hydrogenated castor oil, and polyvinyl alcohol.

The antioxidants can be selected from one or more of sodium bisulfite, potassium bisulfite, sodium sulphate, potassium sulphate, citric acid, dibutylhydroxytoluene, and tert-butylhydroquinone.

The protectives can be selected from one or more of hydroxypropyl methylcellulose, medical sodium hyaluronate, polyacrylamide, carbomer, xylitol, glucose, and alkyl polyglucoside.

The pH regulators can be selected from one or more of sodium dihydrogen phosphate, dibasic sodium phosphate, potassium dihydrogen phosphate, dipotassium phosphate, boric acid, borax, ethanoic acid, sodium acetate, citric acid, trisodium citrate, tartaric acid, potassium sodium tartrate, sodium carbonate, potassium carbonate, sodium bicarbonate, potassium hydrogen carbonate, sodium hydroxide, potassium hydroxide, Triethanolamine, hydrochloric acid, and phosphoric acid.

The preservatives can be selected from one or more of alkyldimethylbenzylammonium chloride, benzyldodecyldimethylammonium bromide, chlorobutanol, and sorbitol.

The composition of the present invention can have other alternative names during actual sales, such as kits, suites, sets, or systems. Two substances in the composition can be mixed and packed together, and can also be packed separately.

The present invention found that the dual staining method with fluorescein sodium and methylene blue can significantly improve the imaging effect. The fluorescein sodium increases the contrast of the background. At the same time, methylene blue can also mark the nucleus very well. The cell form and the nucleus can be clearly observed at once, especially the karyoplasmic ratio change of tumor cells. Therefore, we can clearly determine the normal tissue and tumor tissue to achieve the visualization of the tumor and non-tumor tissue boundary and meet clinical needs. Both dyes have been approved for clinical use and their safety is guaranteed.

In the preferred embodiment, two dyes with different fluorescent wavelength are used for example. It should be understood that tissue can be stained with three or more dyes as long as their identification targets are different and they have different fluorescent wavelengths.

In a further embodiment, fluorescent biomarkers can also be selected from the following dyes: fluorescein isothiocyanate (FITC), phycoerythrin, phycocyanin, allophycocyanin, o-phthalaldehyde, rhodamine and AlexaFluor series dyes, DAPI, Hoechst 33342, thiazole orange, and acridine orange, etc.

In practical application, the staining method of the present invention can not only be applied to histopathologic slides, but also to staining for the live tissue and in vitro culture. Cells waiting for imaging, cells on microcarriers or cells on smears can directly contact with dyes of the present invention, and it is further used in clinical applications such as surgery, diagnosis, and drug delivery, Compared with the prior art, the beneficial effect of the present invention lies in that:

The present invention provides a dual staining method for fluorescent biomarkers used for live-cell imaging. It is fast, efficient, and safe. We can observe the nucleus while observing the cell form. Besides, we can clearly identify normal cells and tumor cells normal cells. It is of great significance for the development of tissue staining, cell morphology, image-guided surgery and other fields.

BRIEF DESCRIPTION OF THE DRAWINGS

FIG. 1 shows the imaging effect comparison of the mouse kidneys stained by only methylene blue, only fluorescein sodium, and dual-stained by methylene blue and fluorescein sodium.

FIG. 2 shows the imaging effect comparison of the mouse livers stained by only methylene blue, only fluorescein sodium, and dual-stained by methylene blue and fluorescein sodium.

FIG. 3 shows the imaging effect comparison of the pig kidneys stained by different fluorescein sodium and methylene blue concentration combinations.

DETAILED DESCRIPTION OF THE INVENTION

Figure 1A:
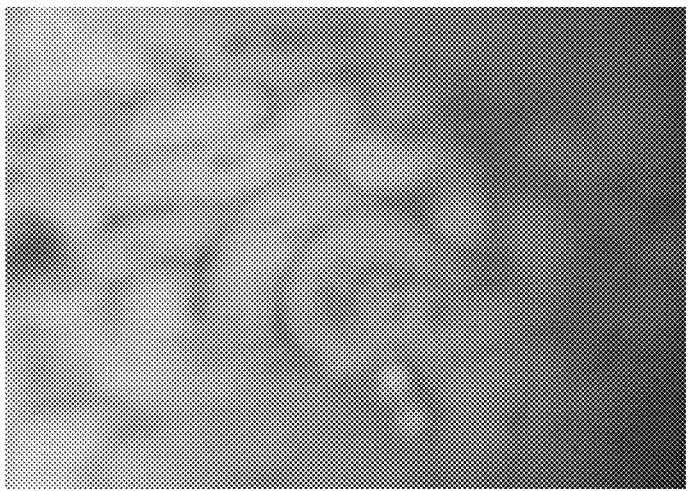
FIG. 1A shows the result of the mouse kidneys only stained by fluorescein sodium and imaged at 470 nm wavelength.
Figure 1B:
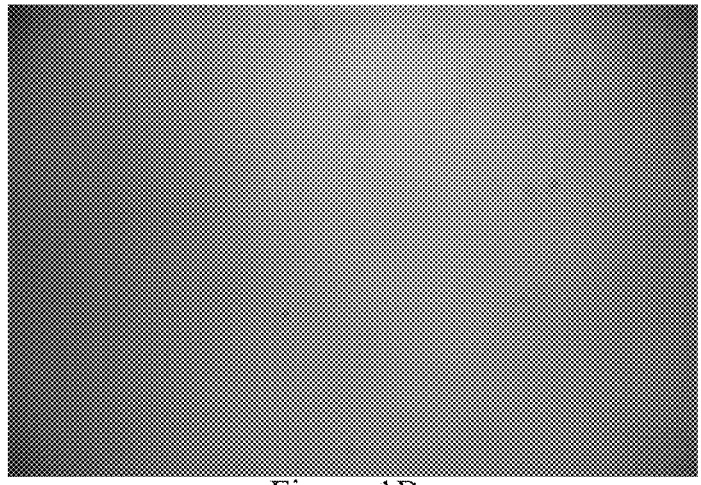
FIG. 1B shows the result of the mouse kidneys only stained by methylene blue and imaged at 470 nm wavelength.
Figure 1C:
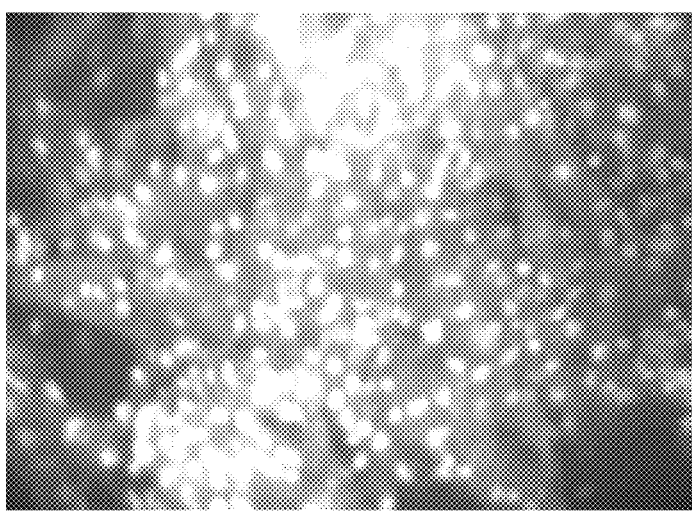
FIG. 1C shows the mouse kidneys only stained by methylene blue and imaged at 660 nm wavelength.
Figure 1D:
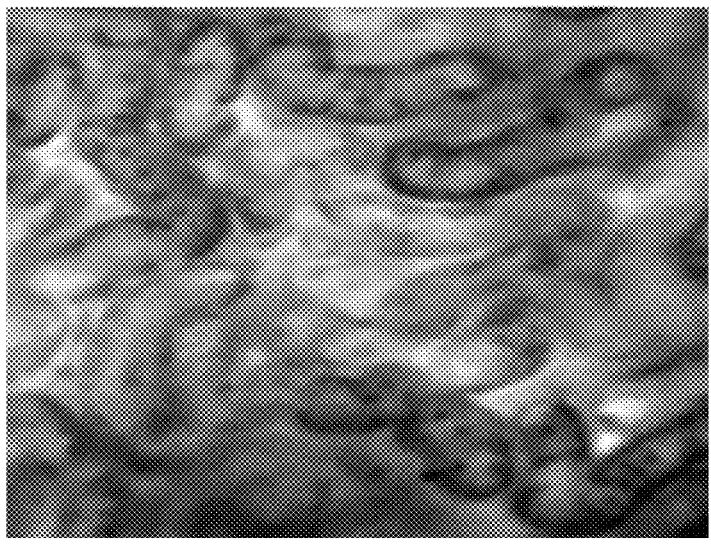
FIG. 1D shows the mouse kidneys dual stained by fluorescein sodium and methylene blue and imaged at 470 nm wavelength.
Figure 1E:
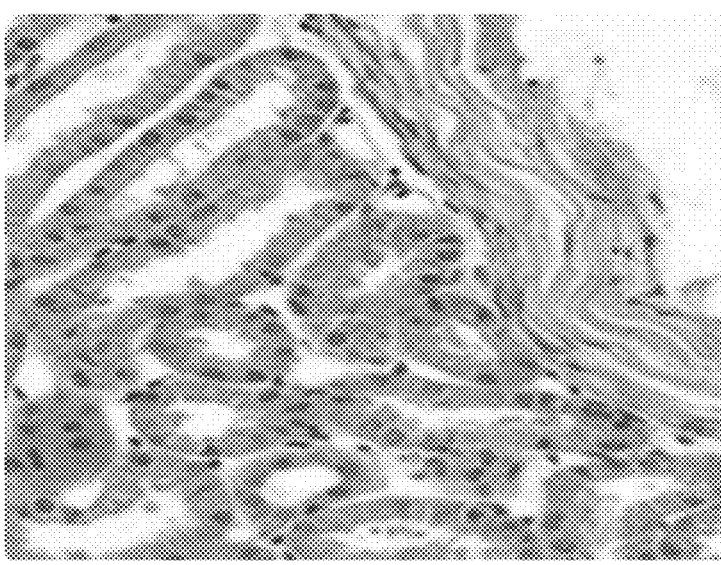
FIG. 1E shows the control of hematoxylin and eosin (HE) stain.
Figure 2A:
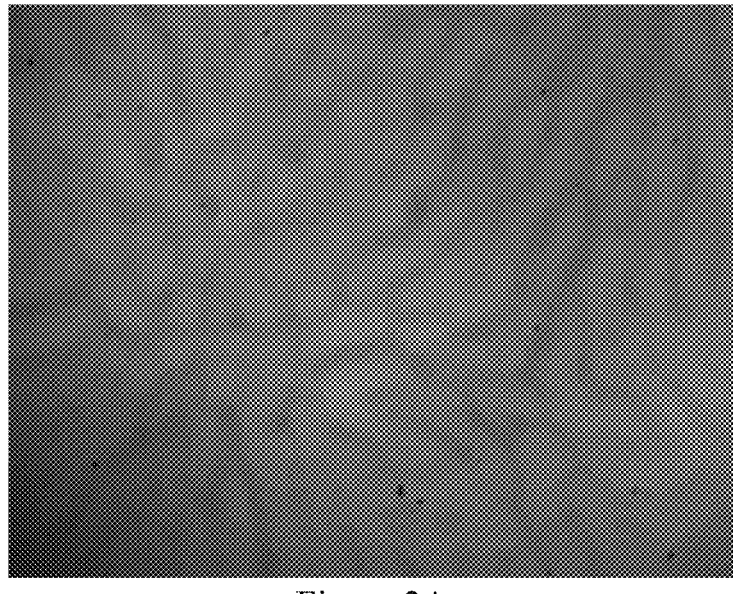
FIG. 2A shows the result of the mouse livers only stained by fluorescein sodium and imaged at 470 nm wavelength.
Figure 2B:
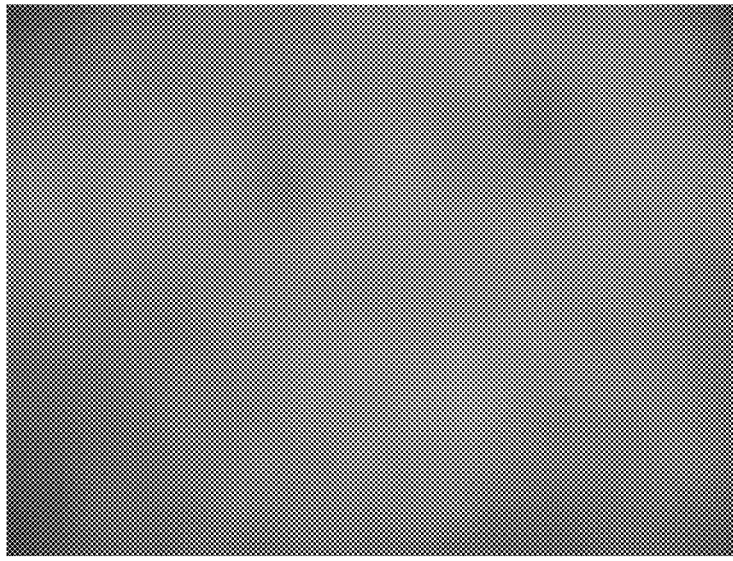
FIG. 2B shows the result of the mouse livers only stained by methylene blue and imaged at 470 nm wavelength.
Figure 2C:
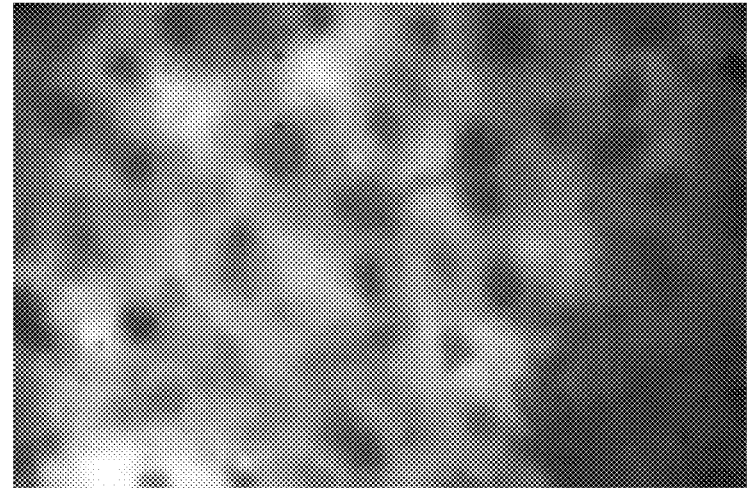
FIG. 2C shows the mouse livers dual stained by fluorescein sodium and methylene blue and imaged at 470 nm wavelength.
Figure 2D:
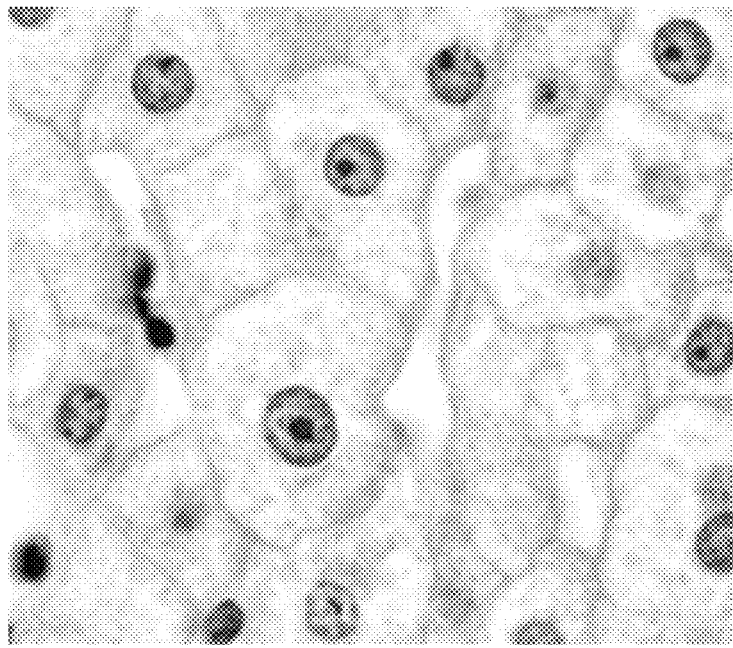
FIG. 2D shows the control of hematoxylin and eosin (HE) stain.
Figure 3A:
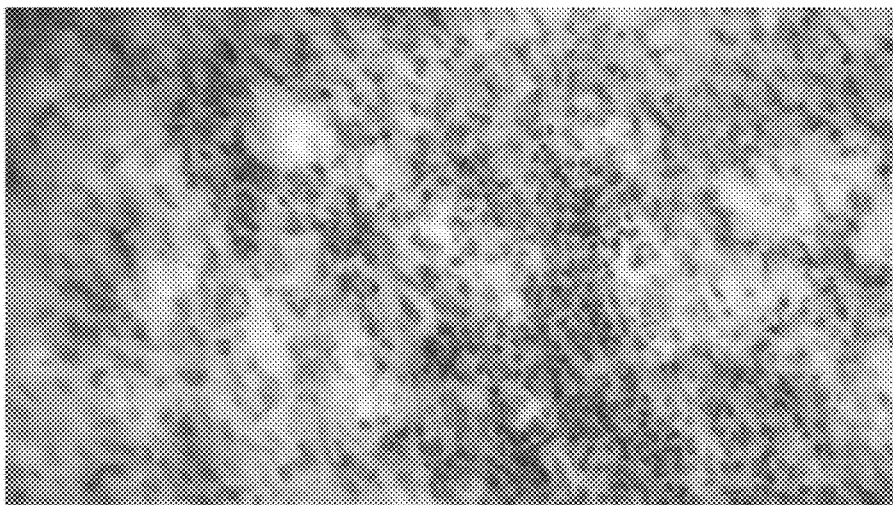
FIG. 3A shows the result of the pig kidneys stained by 0.1% fluorescein sodium+0.5% methylene blue and imaged at 470 nm wavelength.
Figure 3B:
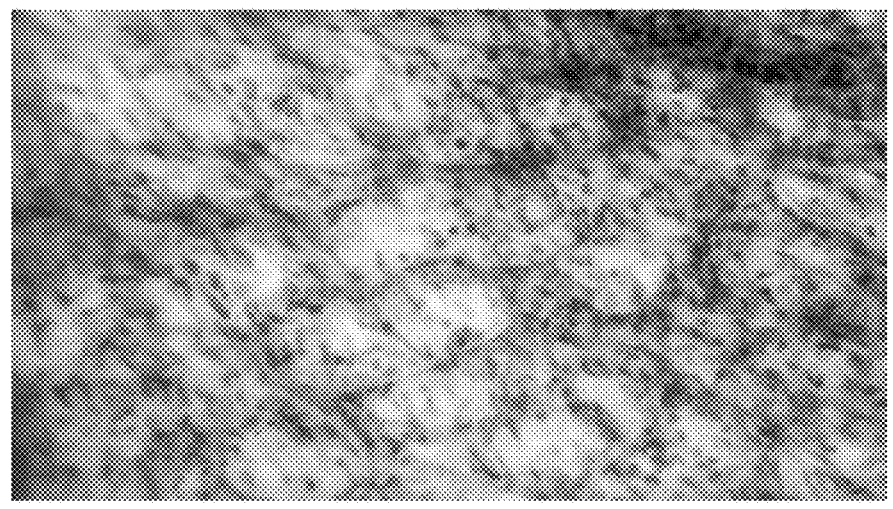
FIG. 3B shows the result of the pig kidneys only stained by 0.25% fluorescein sodium+1% methylene blue and imaged at 470 nm wavelength.
Figure 3C:
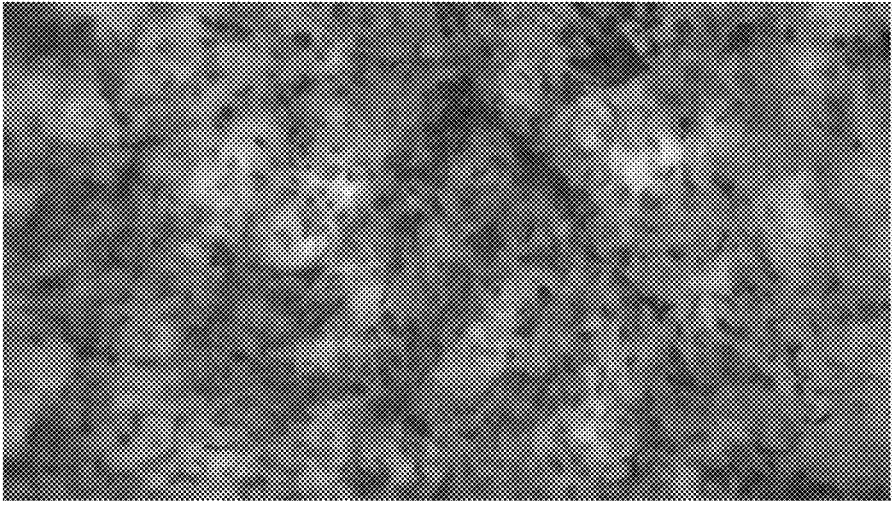
FIG. 3C shows the pig kidneys stained by 0.5% fluorescein sodium+2% methylene blue and imaged at 470 nm wavelength.
Figure 3D:
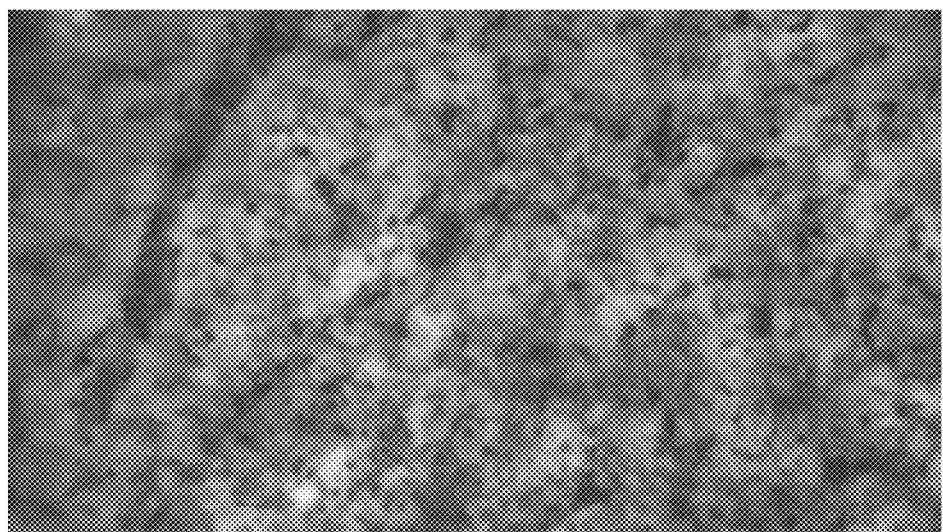
FIG. 3D shows pig kidneys stained by 1% fluorescein sodium+3% methylene blue and imaged at 470 nm wavelength.

The present invention is further described by reference to the following examples. It should be understood that the following embodiments are only used to describe the present invention, rather than limiting the scope of the present invention. In the scope of the invention conception, the changes and advantages which a person skilled in the art can think of are included in the present invention, and the claims and any equivalence are in the protection scope of the present invention. In this specification and the claims of the invention, the meaning of "a," "an and "the includes plural reference unless the context clearly dictates otherwise. The experimental methods that do not indicate the specific conditions in the following examples are general and common knowledge for a person skilled in the art, or according to the conditions recommended by the manufacturer. If there is no specific explanation, all materials and reagents used in the embodiments are commercially available products.

Mice

We used C57BL6 strain mice in the experiments, bought from Model Animal Center of Nanjing University.

Fluorescent Image Analysis

Fluorescent images were obtained by MCI microscope (DiveScope). We observed a sample at 470 nm wavelength after staining the samples. We randomly selected the region of interest for imaging.

Preparation of Staining Agents 0.1% Fluorescein sodium: Weight 0.01 g fluorescein sodium powder, put it into the light avoidance tube, add 10 mL saline, shake it well, wrap the tube with foil paper, and keep away from light.

0.25% Fluorescein sodium: Weight 0.025 g fluorescein sodium powder, put it into the light avoidance tube, add 10 mL saline, shake it well, wrap the tube with foil paper, and keep away from light.

0.5% Fluorescein sodium: Weight 0.05 g fluorescein sodium powder, put it into the light avoidance tube, add 10 mL saline, shake it well, wrap the tube with foil paper, and keep away from light.

1% Fluorescein sodium: Weight 0.1 g fluorescein sodium powder, put it into the light avoidance tube, add 10 mL saline, shake it well, wrap the tube with foil paper, and keep away from light.

0.5% Methylene blue: Weight 0.05 g methylene blue powder, put it into the light avoidance tube, add 10 mL 5% sodium bicarbonate solution, shake it well, wrap the tube with foil paper, and keep away from light.

1% Methylene blue: Weight 0.1 g methylene blue powder, put it into the light avoidance tube, add 10 mL 5% sodium bicarbonate solution, shake it well, wrap the tube with foil paper, and keep away from light.

2% Methylene blue: Weight 0.2 g methylene blue powder, put it into the light avoidance tube, add 10 mL 5% sodium bicarbonate solution, shake it well, wrap the tube with foil paper, and keep away from light.

3% Methylene blue: Weight 0.3 g methylene blue powder, put it into the light avoidance tube, add 10 mL 5% sodium bicarbonate solution, shake it well, wrap the tube with foil paper, and keep away from light.

0.05% 5-ALA (5-aminolevulinic acid): Weight 0.005 g 5-ALA powder, put it into the light avoidance tube, add 10 mL 5% glucose solution, shake it well, wrap the tube with foil paper, and keep away from light.

1% Acriflavine: Weight 0.1 g acrilavine powder, put it into the light avoidance tube, add 10 mL saline, shake it well, wrap the tube with foil paper, and keep away from light.

0.05% ICG indocyanine-green) Weight 0.005 g ICG powder, put it into the light avoidance tube, add 10 mL saline, shake it well, wrap the tube with foil paper, and keep away from light.

0.05% Crystal violet: Weight 0.005 g crystal violet powder, put it into the light avoidance tube, add 10 mL saline, shake it well, wrap the tube with foil paper, and keep away from light.

Example 1. Dual Staining Tissue With Fluorescein Sodium And Methylene Blue 1.1 Mouse Kidney Staining Mice are for tissue staining, and the staining process is as follows:

1. Mice have injected 1% pentobarbital sodium into the abdominal cavity for anesthesia, and the anesthesia dose is 8-9 ml/g.
2. Remove the body fur of the mouse back, cut the epidermis, and expose the kidneys. After removing the kidneys, fix the kidney surface with a blade, and remove the basement membrane on the kidney surface under the microscope with scissors and mules.
3. Use a cotton swab to stop bleeding, apply 0.25% fluorescein sodium to the kidney surface for 2 minutes, wash it with saline three times, and apply 1% methylene blue to the surface staining for 2 minutes. After 2 minutes, we used saline to wash three times, and observed the sample at 470 nm wavelength under the microscope.

FIG. 1 shows the imaging effect comparison of the mouse kidneys stained by only methylene blue, only fluorescein sodium, and dual-stained by methylene blue and fluorescein sodium. FIG. 1A shows the result of the mouse kidneys only stained by fluorescein sodium and imaged at 470 nm wavelength; FIG. 1B shows the result of the mouse kidneys only stained by methylene blue and imaged at 470 nm wavelength. The samples only stained by methylene blue cannot be imaged at 470 nm wavelength. FIG. 1C shows the mouse kidneys only stained by methylene blue and imaged at 660 nm wavelength. FIG. 1D shows the mouse kidneys dual stained by fluorescein sodium and methylene blue and imaged at 470 nm wavelength. We can clearly see the cell contour and the nucleus form of the mouse renal tubules stained by fluorescein sodium and methylene blue. FIG. 1E shows the control of hematoxylin and eosin (HE) stain.

1.2 Mouse Liver Staining

Mice are used for tissue staining, and the staining process is as follows:

1. Mice have injected 1% pentobarbital sodium into the abdominal cavity for anesthesia, and the anesthesia dose is 8-9 ml/g.

2. Remove the body fur of the mouse back, cut the epidermis, and expose the liver. After removing the liver, fix the live surface with a blade.
3. Use a cotton swab to stop bleeding, apply 0.25% fluorescein sodium to the kidney surface for 2 minutes, wash it with saline three times, and apply 1% methylene blue to the surface staining for 2 minutes. After 2 minutes, we used saline to wash three times, and observed the sample at 470 nm wavelength under the microscope.

FIG. 2 shows the imaging effect comparison of the mouse livers stained by only methylene blue, only fluorescein sodium, and dual-stained by methylene blue and fluorescein sodium. FIG. 2A shows the result of the mouse livers only stained by fluorescein sodium and imaged at 470 nm wavelength; FIG. 2B shows the result of the mouse livers only stained by methylene blue and imaged at 470 nm wavelength. The samples only stained by methylene blue cannot be imaged at 470 nm wavelength. FIG. 2C shows the mouse livers dual stained by fluorescein sodium and methylene blue and imaged at 470 nm wavelength. We can clearly see the cell contour and the nucleus form of the livers stained by fluorescein sodium and methylene blue. FIG. 2D shows the control of hematoxylin and eosin (HE) stain.

Based on FIGS. 1 and 2, the imaging effect of dual staining with fluorescein sodium and methylene blue is greatly improved than the imaging effect of only staining with fluorescein sodium or methylene blue. The dual staining with fluorescein sodium and methylene blue improved the contrast to the background. We can clearly observe the tissue and. cell forms, and at the same time, we can also observe the clear nucleus and even the nucleolus. This information will help doctors to examine tumor and non-tumor tissue, bringing more excellent value to medical care.

Example 2. Staining Effect in Different Concentrations of Fluorescein Sodium and Methylene Blue Pig kidneys are used for tissue staining, and the staining process is as follows:

1. Several fresh pig kidneys are purchased and refrigerated at 4° C. in the refrigerator.
2. Wash the fresh pig kidneys with water, and remove the basement membrane on the kidney surface with scissors and mules under a microscope.
3. Apply separately 0.1%, 0.25%, 0.5%, 1% fluorescein sodium to the kidney surface for 1 minute, wash it with saline three times, and then apply separately 0.5%, 1%, 2%, 3% methylene blue to the surface staining for 1 minute. After 1 minute, we used saline to wash three times, and observed the sample at 470 nm wavelength under the microscope.

FIG. 3 shows the imaging effect comparison of the pig kidneys stained by different fluorescein sodium and methylene blue concentration combinations. Among them, FIG. 3A shows the result of the pig kidneys stained by 0.1% fluorescein sodium+0.5% methylene blue and imaged at 470 nm wavelength. FIG. 3B shows the result of the pig kidneys only stained by 0.25% fluorescein sodium+1% methylene blue and imaged at 470 nm wavelength, FIG. 3C shows the pig kidneys stained by 0.5% fluorescein sodium+2% methylene blue and imaged at 470 nm wavelength. FIG. 3D shows pig kidneys stained by 1% fluorescein sodium+3% methylene blue and imaged at 470 nm wavelength.

Based on FIG. 3, different concentrations of fluorescein sodium and methylene blue combination, wherein the concentration of fluorescein sodium is 01%-1%, and the concentration of methylene blue is 0.5%-3%. The combination of the two in the concentration range has a similar staining effect. The combination within this concentration range can clearly distinguish the cell form and the nucleus structure.

Example 3. Dual Staining Tissue with 5-ALA and Acriflavine

Pig livers are used for tissue staining, and the staining process is as follows:

1. Several fresh pig livers are purchased and refrigerated at 4° C. in the refrigerator,
2. Wash the fresh pig livers with water, and remove the basement membrane on the liver surface with scissors and mules under a microscope.
3. Apply 0.05% 5-ALA to the liver surface for 3 minutes, wash it with saline three times, and then apply 1% acriflavine to the surface staining for 2 minutes. After 2 minutes, we used saline to wash three times, and observed the sample at 635 nm wavelength under the microscope.

Figure 4:
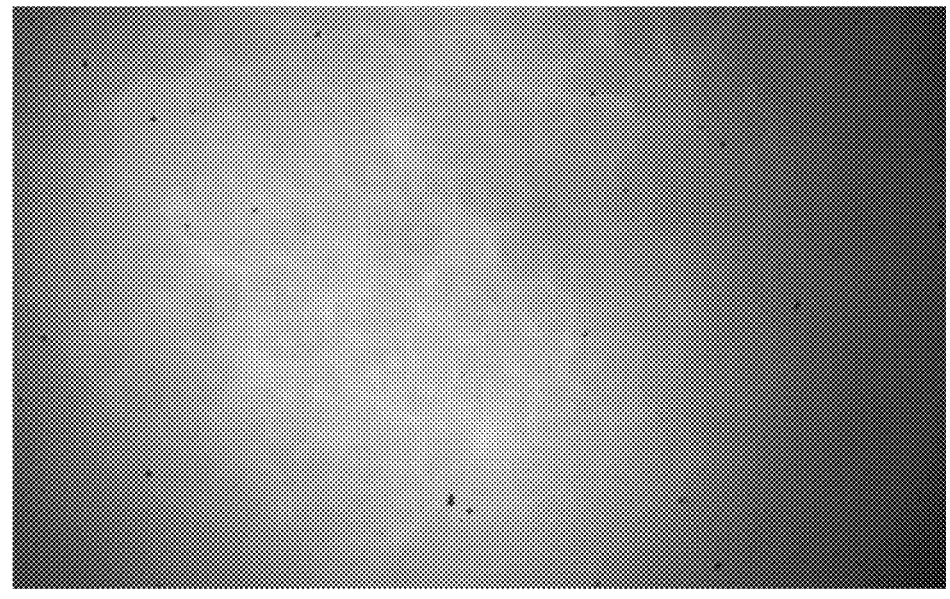
FIG. 4 shows the imaging effect of the pig livers stained by 5-ALA and acriflavine.

FIG. 4 shows the imaging effect of the pig livers stained by 5-ALA and acriflavine. We can clearly see the contour and the nucleus form of the stained liver cells.

Example 4. Dual Staining Tissue with Methylene Blue and ICG

Pig livers are used for tissue staining, and the staining process is as follows:

1. Several fresh pig livers are purchased and refrigerated at 4° C. in the refrigerator.
2. Wash the fresh pig livers with water, and remove the basement membrane on the liver surface with scissors and mules under a microscope.
3. Apply 1% methylene blue to the liver surface for 2 minutes, wash it with saline three times, and then apply 0.05% ICG to the surface staining for 2 minutes. After 2 minutes, we used saline to wash three times, and observed the sample at 835 nm wavelength under the microscope.

Figure 5:
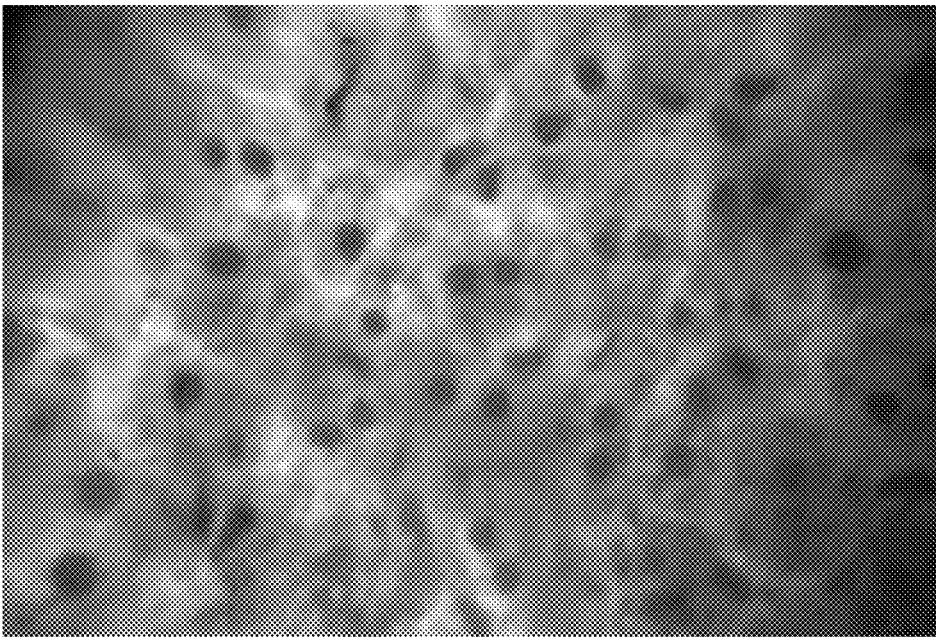
FIG. 5 shows the imaging effect of the pig livers stained by methylene blue and ICG.

FIG. 5 shows the imaging effect of the pig livers stained by methylene blue and ICG. We can clearly see the contour and the nucleus form of the stained liver cells.

Example 5. Dual Staining Tissue with Fluorescein Sodium and Crystal Violet

Pig kidneys are used for tissue staining, and the staining process is as follows:

1. Several fresh pig kidneys are purchased and refrigerated at 4° C. in the refrigerator.
2. Wash the fresh pig kidneys with water, and remove the basement membrane on the kidney surface with scissors and mules under a microscope.
3. Apply 0.25% fluorescein sodium to the kidney surface for 2 minutes, wash it with saline three times, and then apply 0.05% crystal violet to the surface staining for 3 minutes. After 3 minutes, we used saline to wash three times, and observed the sample at 525 nm wavelength under the microscope.

Figure 6:
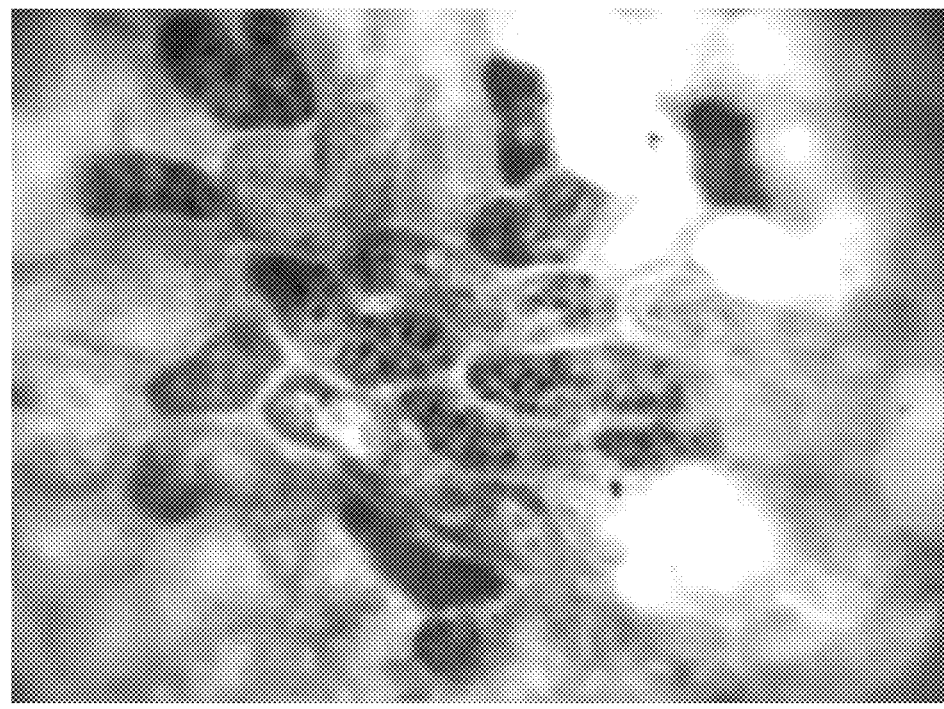
FIG. 6 shows the imaging result of the pig kidneys stained by fluorescein sodium and crystal violet.

FIG. 6 shows the imaging result of the pig kidneys stained by fluorescein sodium and crystal violet. We can clearly see the contour and the nucleus form of the stained liver cells.

All documents mentioned in the present invention are referred to in the full text of this application. In addition, after reading the content mentioned above about the present invention, a person skilled in the art can make various changes or modifications to the present invention. The equivalent amendments also fall in the scope of this application claims.

What is claimed:

1. A staining method for live-cell imaging, wherein said method includes the following steps: simultaneously or separately (i) using a first fluorescent biomarker to stain target cells, which are live cells; (ii) using a second fluorescent biomarker, which is different from the first fluorescent biomarker, to stain the target cells; (iii) using a fluorescent microscope to obtain fluorescent images of the target cells, which can observe the nucleus form while observing the cell contour;

wherein the first biomarker and the second biomarker are selected to ensure that, when using a fluorescent microscope to obtain the fluorescent images of the target cells, the first biomarker enters an exciting state after absorbing incident light energy and emits a first light to show the cell contour in the fluorescent images, and the second biomarker absorbs the first light to show the nucleus form in the fluorescent images.

2. The method according to claim 1, wherein the first fluorescent biomarker has a 460-800 nm excitation wavelength, and the second fluorescent biomarker has a 350-670 nm excitation wavelength.

3. The method according to claim 1, wherein the maximum value of the emission spectrum of the second fluorescent biomarker is at least 50 nm different from the maximum value of the excitation spectrum of the said first fluorescent biomarker.

4. The method according to claim 1, wherein the first fluorescent biomarker is selected from fluorescein sodium, 5-aminolevulinic acid, and indocyanine green; the second biomarker is selected from methylene blue, acriflavine and crystal violet.

5. The method according to claim 4, wherein the first biomarker is 5-aminolevulinic acid, and the second biomarker is acriflavine.

6. The method according to claim 4, wherein the first biomarker is indocyanine green, and the second biomarker is crystal violet.

7. The method according to claim 1, wherein the first biomarker is fluorescein sodium, the second biomarker is methylene blue, and the live cells are tumor cells.

8. The method according to claim 1, wherein the method is applied to live tissue staining.

9. The method according to claim 1, wherein the live cells include tumor cells.

10. A composition for live cell staining, wherein said composition includes the first biomarker and the second biomarker according to claim 1.

11. The composition according to claim 10, wherein the first biomarker is fluorescein sodium, and the second biomarker is methylene blue.

12. The composition according to claim 10, wherein the first biomarker is 5-aminolevulinic acid, and the second biomarker is acriflavine.

13. The composition according to claim 10, wherein the first biomarker is indocyanine green, and the second biomarker is crystal violet.

14. The composition according to claim 10, wherein said composition further also includes stabilizers, antioxidants, protectives, preservatives, and pH regulators.

15. A method for diagnosing tumor in a mammal comprising the method of claim 1.

* * * * *